United States Patent
Tsujimoto et al.

(10) Patent No.: US 9,351,815 B2
(45) Date of Patent: May 31, 2016

(54) CURABLE COMPOSITION AND CURED PRODUCT FOR DENTAL USE

(75) Inventors: Masaya Tsujimoto, Ehime (JP); Mikio Sakaguchi, Wakayama (JP)

(73) Assignees: PANASONIC HEALTHCARE CO., LTD., Ehime (JP); KAO CORPORATION, Tokyo (JP)

( * ) Notice: Subject to any disclaimer, the term of this patent is extended or adjusted under 35 U.S.C. 154(b) by 392 days.

(21) Appl. No.: 13/640,773

(22) PCT Filed: Apr. 13, 2011

(86) PCT No.: PCT/JP2011/059144
§ 371 (c)(1),
(2), (4) Date: Oct. 12, 2012

(87) PCT Pub. No.: WO2011/129355
PCT Pub. Date: Oct. 20, 2011

(65) Prior Publication Data
US 2013/0030082 A1  Jan. 31, 2013

(30) Foreign Application Priority Data
Apr. 13, 2010 (JP) ................................. 2010-091981

(51) Int. Cl.
| | | |
|---|---|---|
| A61K 6/083 | (2006.01) | |
| A61C 13/087 | (2006.01) | |
| C01B 33/12 | (2006.01) | |
| C01B 33/18 | (2006.01) | |
| A61K 6/027 | (2006.01) | |
| A61K 6/00 | (2006.01) | |

(52) U.S. Cl.
CPC ............ *A61C 13/087* (2013.01); *A61K 6/0091* (2013.01); *A61K 6/0276* (2013.01); *A61K 6/083* (2013.01); *C01B 33/12* (2013.01); *C01B 33/18* (2013.01); *A61K 6/0005* (2013.01); *A61K 6/0088* (2013.01); *C01P 2004/61* (2013.01); *C01P 2004/62* (2013.01)

(58) Field of Classification Search
CPC ... A61K 6/083; A61K 6/0005; A61K 6/0088; C01P 2002/74; C08L 33/08; C08L 33/10
USPC ........................................................ 523/115
See application file for complete search history.

(56) References Cited

U.S. PATENT DOCUMENTS

| | | |
|---|---|---|
| 4,503,169 A | 3/1985 | Randklev |
| 2002/0022677 A1 | 2/2002 | Teramae et al. |
| 2003/0089276 A1* | 5/2003 | Nishida et al. .................. 106/35 |

FOREIGN PATENT DOCUMENTS

| | | |
|---|---|---|
| JP | 60-233007 | 11/1985 |
| JP | 07-048118 | 2/1995 |
| JP | 07-206983 | 8/1995 |
| JP | 11-132421 | 5/1999 |
| JP | 2000-063636 | 2/2000 |
| JP | 2000-205523 | 7/2000 |
| JP | 2000-346318 | 12/2000 |
| JP | 2001-302429 | 10/2001 |
| JP | 2002-038028 | 2/2002 |
| JP | 2002-114620 | 4/2002 |
| JP | 2003-176120 | 6/2003 |
| JP | 3481660 | 12/2003 |
| JP | 2004-203664 | 7/2004 |
| JP | 2005-231973 | 9/2005 |

OTHER PUBLICATIONS

U.S. Appl. No. 13/640,768 to Masaya Tsujimoto et al., filed Oct. 12, 2012.
Savitzky et al., "Smoothing and Differentiation of Data by Simplified Least Squares Procedures", Analytical Chemistry, 36(8), Jul. 1964, pp. 1627-1639.
Sonneveld et al., "Automatic Collection of Powder Data from Photographs", J. Appl. Cryst. 8,1, 1975, pp. 1-7.
Search report from International Application No. PCT/JP2011/059144, mail date is Jul. 19, 2011.
Japanese office action in JP 2010-091981, dated May 27, 2014.

* cited by examiner

*Primary Examiner* — Michael Pepitone
(74) *Attorney, Agent, or Firm* — Greenblum & Bernstein, P.L.C.

(57) ABSTRACT

The present invention provides a curable composition allowing a cured product having high aesthetic quality, strength and durability along with having high surface lubricating property to be formed. The curable composition according to the present invention comprises: an inorganic powder and a polymerizable monomer. The inorganic powder contains a spherical crystallization control powder. The spherical crystallization control powder has a silicon dioxide content in the range of 97 to 100 mass %. An amorphous portion and a crystalline portion are mixed within the spherical crystallization control powder. A refractive index difference is not more than 0.05 between the spherical crystallization control powder and a cured product obtained by curing only constituents other than the spherical crystallization control powder.

8 Claims, No Drawings

CURABLE COMPOSITION AND CURED PRODUCT FOR DENTAL USE

CROSS REFERENCE TO RELATED APPLICATIONS

This application is a U.S. national stage application of PCT/JP2011/059144, filed Apr. 13, 2011, which claims priority to Japanese patent application 2010-091981, filed Apr. 13, 2010.

TECHNICAL FIELD

The present invention relates to a curable composition and a cured product for dental use formed from this curable composition.

BACKGROUND ART

In order to obtain teeth crown materials, prosthetic materials, artificial teeth and the like for dental use (hereafter, collectively referred to as dental materials), generally, curable compositions and cured product thereof are used, containing an inorganic powder such as silica (silicon dioxide), a polymerizable monomer of the (meth)acrylate series, a photopolymerization catalyst or a heat-curing catalyst and the like. Aesthetic quality, strength, durability and the like are demanded of such dental materials so as to be used as alternative to natural teeth. In prior art, the use of a variety of inorganic powders has been proposed to confer a variety of capabilities to dental materials.

For instance, Patent Reference 1 describes a filler for dental composite in which silicon dioxide and another metal oxide are aggregated and then heat-treated at a lower temperature than the crystallization temperature of this oxide, to thereby form independent amorphous layers with silicon dioxide and the other metal oxide.

Patent Reference 2 describes a dental complex composition comprising a polymerizable monomer, a filler and a polymerization initiator, wherein a heat-treated aggregate of silica and another metal oxide, of which average particle size, refractive index, pore volume, BET specific surface area and primary particle size are controlled, is used as the filler.

Patent Reference 3 described a dental filling glass which contains $SiO_2$, $B_2O_3$, $Al_2O_3$, $P_2O_5$, BeO, MgO, CaO, X-ray contrasting element oxide, alkaline metal oxide, and F in specific proportions, and in which Si, B and Al elements forming the glass framework are contained at specific molar ratios.

PRIOR ART REFERENCES

Patent References

Patent Reference 1: Japanese Patent Publication No. 3481660
Patent Reference 2: Japanese Patent Application Publication No. 2001-302429
Patent Reference 3: Japanese Patent Application Publication No. 2002-114620

DISCLOSURE OF THE INVENTION

Problems to be Solved by the Invention

However, along with aesthetic quality, strength and durability, high surface lubricating property is also demanded of dental materials such that they are fixed inside the mouth cavity. Prior art dental materials, however, do not have these properties sufficiently.

In other words, with the arts described in Patent References 1 and 2, the strength of the portion where silicon dioxide and another metal oxide are aggregated is reduced, thereby causing a problem that the strength of a resulting cured product is insufficient.

In addition, with the art described in Patent Reference 3, only granular type powder can be obtained as dental filling glass, and therefore a cured product of a curable composition containing such dental filling glass has the problem that the surface lubricating property becomes low.

The present invention was made in view of the above circumstances, and an object thereof is to provide a curable composition allowing a cured product having high aesthetic quality, strength and durability along with having high surface lubricating property to be formed, and a cured product for dental use obtained by curing this curable composition.

Means for Solving the Problems

The curable composition according to a first invention is a curable composition comprises: an inorganic powder and a polymerizable monomer, wherein the inorganic powder comprises a spherical crystallization control powder, the spherical crystallization control powder has a silicon dioxide content in the range of 97 to 100 mass %, an amorphous portion and a crystalline portion are mixed within the spherical crystallization control powder, and a refractive index difference is not more than 0.05 between the spherical crystallization control powder and a cured product obtained by curing only constituents other than the spherical crystallization control powder in the curable composition.

In the first invention, a refractive index of the spherical crystallization control powder may be in the range of 1.48 to 1.60.

In the first invention, a relative background level of the spherical crystallization control powder in an x-ray diffraction spectrum may be 3 to 10.

In the first invention, an average particle size of the spherical crystallization control powder may be in the range of 0.01 to 50 µm.

In the first invention, the spherical crystallization control powder may be obtained by partially crystallizing, through heat treatment, amorphous spherical particles obtained by a flame fusion method.

In the first invention, a polymerization catalyst may be further comprised, and the spherical crystallization control powder content may be in the range of 5 to 95 mass %.

In the first invention, the polymerizable monomer may comprise at least one of an acrylate monomer and a methacrylate monomer, and the spherical crystallization control powder content may be in the range of 55 to 95 mass %.

The cured product for dental use according to a second invention is obtained by curing the curable composition according to the first invention.

Effects of the Invention

According to the present invention, it is possible to obtain a curable composition that can form a cured product with a surface lubricating property as well as high aesthetic quality, strength and durability.

In addition, according to the present invention, it is possible to obtain a cured product for dental use with high surface lubricating property as well as high esthetic quality, strength and durability.

BEST MODE FOR CARRYING OUT THE INVENTION

In the present embodiment, the curable composition contains an inorganic powder and a polymerizable monomer. This inorganic powder contains a spherical crystallization control powder. The spherical crystallization control powder has silicon dioxide as the main constituent, silicon dioxide content is in the range of 97 mass % to 100 mass %. Additionally, in this spherical crystallization control powder, an amorphous portion and a crystalline portion are mixed within one particle. Furthermore, the refractive index difference is not more than 0.05 between this spherical crystallization control powder and the cured product obtained when only the constituents after removing the spherical crystallization control powder in the curable composition are cured (hereafter referred to as partially cured product in order to distinguish from cured product of curable composition containing the spherical crystallization control powder).

As mentioned above, the difference between the refractive index of the spherical crystallization control powder and the refractive index of the partially cured product is not more than 0.05. In particular, it is desirable that the refractive index of the spherical crystallization control powder is in the range of 1.48 to 1.60. The reason is that the refractive indices of cured products of polymerizable monomers such as acrylate monomers and methacrylate monomers used for dental applications are generally in this range.

The refractive index of the spherical crystallization control powder is influenced heavily by the proportion of amorphous portion and crystalline portion within the spherical crystallization control powder. The relative background level in the x-ray diffraction spectrum of the spherical crystallization control powder serves as an index of the proportion of the amorphous portion and the crystalline portion within the spherical crystallization control powder. The larger the relative background level, the larger the proportion of amorphous portion present within the spherical crystallization control powder, and the smaller the relative background level, the larger the proportion of the crystalline portion present within the spherical crystallization control powder.

The relative background level in the x-ray diffraction spectrum of the spherical crystallization control powder is represented by the ratio (F/A) between the background level (F) of the x-ray diffraction spectrum of the spherical crystallization control powder and the background level (A) of the x-ray diffraction spectrum of the standard sample, when the respective x-ray diffraction spectra of the spherical crystallization control powder and the crystalline standard sample are measured with identical conditions. The background level is the mean value of the diffraction intensity of the background portion in an x-ray diffraction spectrum.

The background level (F) of the spherical crystallization control powder is derived from the following mathematical formula (1), based on the powder x-ray diffraction spectrum measured using a Cu-Kα beam.

[Math 1]

$$F = \frac{\sum_{2\theta=10}^{35} (\text{Diffraction Intensity})}{N} \quad (1)$$

(Diffraction Intensity)

Denominator N in the right member of mathematical formula (1) is the number of diffraction intensity measurement points for the background portion in a range of 2θ=10 to 35°, which number is 1,501. The numerator in the right member of formula (1) represents the sum of diffraction intensities at each of the 1,501 measurement points.

The background level (A) of the standard sample is derived by the same method as for the spherical crystallization control powder, using for instance a standard alumina powder (National Institute of Standard & Technology, Standard Reference Material 674a) as the standard sample.

The value (F/A) obtained by dividing the background level (F) of the spherical crystallization control powder derived as described above by the background level (A) of the standard sample is the relative background level. From the point of view of bringing the refractive index to at least 1.48 and the point of view of increasing the hardness of the spherical crystallization control powder per se to increase the hardness of the cured product into which the spherical crystallization control powder is added, the relative background level is preferably not more than 10.0, more preferably not more than 7.5 and even more preferably not more than 7.0. In addition, from the point of view of increasing the transparency of the spherical crystallization control powder per se and the point of view of suppressing the abrasion of the mold at forming time to reduce contamination, at least 3.0 is desirable, at least 3.5 is more desirable and at least 4.0 is even more desirable. That is to say, taking these points of view together, a relative background level of 3.0 to 10.0 is desirable, 4.0 to 7.5 is more desirable and 5.0 to 7.0 is even more desirable. Regarding controlling the relative background level to be in the ranges described above, the relative background level can be reduced by increasing the addition amount of at least one of an alkaline metal compound and an alkaline earth metal compound, by elevating the heat treatment temperature or by extending the heat treatment time, in the production method described below.

If the surface is formed from a roughly curved surface, the particle shape of the spherical crystallization control powder does not need to be a rigorous sphere. However, from the point of view of increasing the dispersibility of the spherical crystallization control powder inside the curable composition thereby allowing for a high filling into the curable composition, the point of view of suppressing light scattering by the spherical crystallization control powder to increase the transparency of the cured product, the point of view of improving the surface lubricating property of the cured product, and the like, the sphericity of particles in the spherical crystallization control powder is preferably at least 0.95. This sphericity is more desirable if at least 0.96 and even more desirable if at least 0.97. Regarding controlling the sphericity to be in the ranges described above, the sphericity can be raised by elevating the flame temperature or by extending the in-flame residence time, in the production method described below.

Regarding calculation of sphericity, from the surface area of a projected cross-section of each particle and the perimeter length of this cross-section of each particle which are obtained based on microphotographic images of particles in the spherical crystallization control powder, the value of (circumferential length of a true circle of the same surface area as the surface area of a particle projection cross-section)/(measurement value of the perimeter length of the particle projection cross-section) is calculated. The mean value of the values respectively derived for 50 arbitrary particles in the spherical crystallization control powder serves as the sphericity.

The curable composition may further contain an inorganic powder other than the spherical crystallization control powder in a range that does not compromise the effects of the present invention. As this inorganic powder other than the spherical crystallization control powder, nano-size silica, alumina, zirconia and the like may be cited. If the inorganic powder other than the spherical crystallization control powder is nano-sized, the transparency of the cured product for dental use is not compromised while the strength and the durability thereof are improved. From the point of view of improving the surface lubricating property of the cured product for dental use, it is desirable that the shape of the inorganic powder other than the spherical crystallization control powder is also spherical.

The content of the spherical crystallization control powder in the entire amount of inorganic powder is preferably defined as at least 50 mass %, more preferably as at least 75 mass %, and yet more preferably as at least 85 mass %. The upper limit of the content is 100 mass %.

A spherical crystallization control powder is obtained with a natural compound or a synthetic compound serving as raw material. Inorganic minerals having silicon dioxide as the main constituent may be cited as natural compounds. The synthetic compound is obtained, for instance, by spheroidizing a starting material by the flame fusion method. Herein, the starting material is obtained from a natural stone such as silica stone by the wet-milling, the dry-milling, or the like. In addition, the synthetic compound can also be obtained by the sol-gel method, or the like. In the following, the spherical crystallization control powder that is a synthetic compound will be described in further detail.

The spherical crystallization control powder is obtained for instance by performing a treatment by the flame fusion method to the starting material. The flame fusion method is a method whereby starting materials such as the pulverized powder of an inorganic constituent is melted in a flame and spheroidized. The starting material may be a crushed material or spherical powder, and may also be a mixture of the crushed material and spherical powder. By this flame fusion method, melted starting material spheroidizes due to surface tension. With this flame fusion method, a spherical crystallization control powder having a suitable degree of particle size is obtained readily.

As the starting materials, materials that are silica sources may be cited, such as silica stone, silica sand, quartz, cristobalite, amorphous silica, fumed silica, ethyl silicate and silica sol. In a preferred mode, the starting material is introduced into the flame in a dispersed state in a carried gas such as oxygen. The flame is generated for instance by burning oxygen and fuel such as propane, butane, methane, liquefied natural gas, LPG, heavy oil, kerosene, gas oil and pulverized coal. From the point of view of generating a high temperature flame, it is desirably to employ an oxygen gas burner. The structure of the burner is not limited in particular, and well-known burners can be used such as described in Japanese Patent Application Publication No. 07-48118, Japanese Patent Application Publication No. 11-132421, Japanese Patent Application Publication No. 2000-205523, or Japanese Patent Application Publication No. 2000-346318. Spherical crystallization control powder having high sphericity is obtained by such flame fusion methods. From the point of view of securing sufficient dispersibility of the starting material, a concentration of starting material in the carrier gas is desirably in the range of 0.1 to 20 kg/Nm$^3$, and more desirably in the range of 0.2 to 10 kg/Nm$^3$.

The spherical crystallization control powder may be obtained by other methods than the flame fusion method, for instance, sol-gel method and the like.

A spherical crystallization control powder obtained by the flame fusion method or the sol-gel method is generally amorphous. By performing heat treatment on this amorphous spherical crystallization control powder in conditions giving rise to partial crystallization, a portion that is amorphous and a portion that is crystalline become mixed within each particle in the spherical crystallization control powder. Furthermore, the proportions of the portion that is amorphous and the portion that is crystalline within the particle are readily controlled by this heat treatment. As a result, the refractive index of the spherical crystallization control powder is also readily adjusted.

In particular, if a treatment by the flame fusion method and a subsequent heat treatment are adopted, the spherical crystallization control powder becomes readily adjusted to a suitable degree of particle size. Further, by adjusting the heat treatment conditions suitably, a spherical crystallization control powder having the desired relative background level (that is to say, the desired proportions of amorphous portion and crystalline portion) and having the desired refractive index is obtained readily.

From the point of view of not melting the spherical crystallization control powder, a processing temperature of not more than 1,700° C. during heat treatment is desirable, not more than 1,400° C. is more desirable and not more than 1,100° C. is even more desirable. In addition, from the point of view of promoting partial crystallization of the spherical crystallization control powder to increase productivity, at least 600° C. is desirable, at least 800° C. is more desirable and at least 1,000° C. is even more desirable, for this processing temperature. When these points of view are taken together, a processing temperature of 600 to 1,700° C. is desirable, 800 to 1,400° C. is more desirable and 1,000 to 1,100° C. is even more desirable.

The processing time during heat treatment is suitably determined in relation to the processing temperature. If the processing temperature is high, crystallization is promoted in a short processing time, rising the refractive index of the spherical crystallization control powder. From the point of view of promoting crystallization and increasing the refractive index, a processing time of at least 0.01 hours is desirable and at least 0.5 hours is more desirable. In addition, from the point of view of increasing productivity, a processing time of not more than 100 hours is desirable and not more than 24 hours is more desirable. When these points of view are taken together, a processing time of 0.01 to 100 hours is desirable and 0.5 to 24 hours is more desirable.

From the point of view of promoting crystallization of spherical crystallization control powder by heat treatment, it is desirable to add to the spherical crystallization control powder prior to heat treatment one or more species of compounds chosen from alkaline metal compounds and alkaline earth metal compounds as crystallization promoters. As the compounds mentioned above, those with high water solubility are desirable, and chlorides, carbonates, nitrates, sulfates or oxides such as of sodium, potassium, magnesium or calcium, or complex oxides such as calcium silicate, aluminum silicate and magnesium aluminate, and the like may be cited. Among these, using calcium nitrate as the compound mentioned above is desirable from the point of view of crystallization promotion.

From the point of view of promoting crystallization of the spherical crystallization control powder while suppressing melting and adhesion during heat treatment, the amount added of this crystallization promoter is preferably at least 0.10 parts by mass in terms of the oxides of the metal elements (alkaline metal elements and alkaline earth metal elements) in the crystallization promoter with respect to 100 parts by mass of spherical crystallization control powder, with at least 0.15 parts by mass being more desirable and at least 0.20 parts by mass being even more desirable. In addition, from the point of view of suppressing a decrease in transparency of the spherical crystallization control powder due to impurities as well as the point of view of increasing the sphericity of the spherical crystallization control powder, the amount added of the crystallization promoter is preferably not more than 3 parts by mass in terms of the oxides of the metal elements (alkaline metal elements and alkaline earth metal elements) in the crystallization promoter with respect to 100 parts by mass of spherical crystallization control powder, with not more than 2 parts by mass being more desirable and not more than 1.5 parts by mass being even more desirable. When these points of view are taken together, 0.10 to 3 parts by mass is desirable for the crystallization promoters of the above compounds in terms of the oxides of the metal elements (alkaline metal elements and alkaline earth metal elements) in the crystallization promoter with respect to 100 parts by mass of spherical crystallization control powder, with 0.15 to 2 parts by mass being more desirable and 0.20 to 1.5 parts by mass being even more desirable.

From the point of view of elevating the refractive index, the total of the contents in the oxides of the alkaline metals and the alkaline earth metals in the spherical crystallization control powder is preferably at least 0.10 mass %, with at least 0.15 mass % being more desirable and at least 0.20 mass % being even more desirable. In addition, from the point of view of suppressing a decrease in the transparency of the spherical crystallization control powder per se due to impurities to increase the transparency of the cured product containing the spherical crystallization control powder and the point of view of improving the sphericity of the spherical crystallization control powder, not more than 2.9 mass % is desirable, not more than 2.0 mass % is more desirable and not more than 1.5 mass % is even more desirable. That is to say, when these points of view are taken together, for the total of the oxides of the alkaline metal compounds and the alkaline earth metal compounds in the spherical crystallization control powder, 0.10 to 2.9 mass % is desirable, 0.15 to 2.0 mass % is more desirable and 0.20 to 1.5 mass % is even more desirable.

The average particle size of the spherical crystallization control powder is preferably in a range of 0.01 to 50 μm. If the average particle size of the spherical crystallization control powder is at least 0.01 μm, the increase in the viscosity of the curable composition containing this spherical crystallization control powder is suppressed, and in addition, mixing spherical crystallization control powder in large amounts in the curable composition without provoking an increase in the viscosity of the curable composition becomes possible. Moreover, the strength of the cured product of the curable composition increases further. In addition, if the average particle size of the spherical crystallization control powder is not more than 50 μm, the surface lubricating property of the cured product increases further. For the average particle size of the spherical crystallization control powder, 0.1 to 20 μm is more desirable and 1 to 10 μm is even more desirable. To control the average particle size to be in the ranges described above, it suffices to adjust the particle size of the raw material particles introduced into the flame in the production method described below.

It is desirable for the spherical crystallization control powder to have undergone a surface treatment by a coupling agent. The coupling agent may be mixed and combined into the curable composition. In the case of a spherical crystallization control powder to be included in a curable composition for obtaining a dental material, it is desirable to use a coupling agent that is used generally for dental use. Well-known coupling agents such as for instance γ-methacryloxypropyl trimethoxysilane and vinyl trimethoxysilane may be cited as coupling agents.

The curable composition contains a polymerizable monomer. In particular, as polymerizable monomers to be included in a curable composition for obtaining a dental material, well-known polymerizable monomers generally used in dental applications may be cited, such as acrylate monomers, methacrylate monomers, urethane acrylate monomers, urethane methacrylate monomers, acrylate monomers containing a bisphenol A backbone and methacrylate monomers containing a bisphenol A backbone. As concrete examples of these polymerizable monomers, compounds such as methyl acrylate, methyl methacrylate, 2-hydroxyethyl acrylate, 2-hydroxyethyl methacrylate, triethyleneglycol diacrylate, triethyleneglycol dimethacrylate, di(phenylglycidylether acrylate)-hexamethylene diurethane, di-2-methacryloxyethyl-2,2,4-trimethyl hexamethylene diurethane (UDMA), 2,2-bis(4-(3-methacryloyloxy-2-hydroxypropoxy)phenyl) propane (Bis-GMA), trimethylolpropane triacrylate and trimethylol propane trimethacrylate may be cited. Among these compounds, one species alone may be used or a plurality of species may be used in combination.

In addition, such compounds as epoxy resin monomers such as bisphenol A diglycidylether, which are generally used for electronic material use, may be used as polymerizable monomers.

As necessary, the curable composition may contain a polymerization catalyst. In particular, as polymerization catalysts to be included in a curable composition for obtaining a dental material, well-known polymerization catalyst generally used for dental use may be cited, such as heat polymerization initiators and photopolymerization initiators. As concrete examples of these polymerization catalysts, heat polymerization initiators such as benzoylperoxide, tertiary butylperoxide and methylethylketone peroxide, photopolymerization initiators such as camphor quinone, benzoin, and benzophenone, and the like, may be cited. Among these compounds, one species alone may be used or a plurality of species may be used in combination.

As necessary, the curable composition may further contain an additive like a polymerization inhibitor, an oxidation inhibitor, an ultraviolet light absorbent, a light stabilizer, an antibacterial agent, a controlled fluorine release agent, a color pigment, and/or other conventionally well-known additive. In particular, suitable compounds that are in general for dental use are used as additives to be included in a curable composition for obtaining a dental material.

The spherical crystallization control powder content in the curable composition is preferably in a range of 5 to 95 mass %. If the spherical crystallization control powder content is at least 5 mass % in this way, cured product-reinforcement effect by the inorganic powder starts to manifest itself, and in addition, if this content is not more than 95 mass %, uniform mixing of the spherical crystallization control powder into the entirety of the composition is facilitated. It is more desirable if this spherical crystallization control powder content is in the range of 40 to 95 mass % and particularly desirable if in a range of 55 to 95 mass %.

Such a curable composition is light-cured, heat-cured or the like, to obtain a cured product. Owing to this cured product containing such spherical crystallization control powder as described above, in which amorphous silicon dioxide and crystalline silicon dioxide are mixed, the refractive index difference is not more than 0.05 between the spherical crystallization control powder and the partially cured product in the cured product. Therefore, this cured product exhibits sufficiently high transparency. Moreover, the refractive index of the spherical crystallization control powder is adjusted readily by having the proportions of amorphous silicon dioxide and crystalline silicon dioxide in the spherical crystallization control powder adjusted. Therefore, even in case a composition in the curable composition other than the spherical crystallization control powder is modified, a high transparency cured product is obtained by a spherical crystallization control powder having an appropriate refractive index being used. The smaller the refractive index difference between the partially cured product and the spherical crystallization control powder, the higher the transparency of the cured product.

For the transparency of a cured product used in dental application, the range of 40% to 95% is desirable, the range of 50% to 95% is more desirable and the range of 60% to 95% is particularly desirable, in the evaluation method by the transparency test described below.

In addition, owing to the spherical crystallization control powder being spherical, the surface lubricating property of the cured product becomes high, therefore, scratching the mouth cavity or a tooth becomes unlikely even if this cured product is fixed inside the mouth cavity.

In addition, since a spherical crystallization control powder that is highly uniform is contained in the cured product, compared to such cases where heterogeneous particles aggregate inside the cured product, the cured product may exert high strength and durability.

Furthermore, since silicon dioxide has high safety with respect to living organisms, the safety of the cured product with respect to living organisms also becomes higher.

Owing to the existence of such advantages as described above, the cured product formed from the curable composition is suitable as a cured product for dental use for forming teeth crown material, prosthetic material, artificial teeth and the like. That is to say, the curable composition is suitable for forming a cured product for dental use. In particular, if the refractive index difference is not more than 0.02 between the partially cured product and the spherical crystallization control powder, a cured product for dental use having an extremely close transparency to natural teeth is obtained. It is even more desirable if this refractive index difference is not more than 0.01.

From the point of view of approximating the refractive index of the constituents excluding the spherical crystallization control powder to improve the optical transparency of the cured product added with the spherical crystallization control powder, it is desirable that the refractive index of the spherical crystallization control powder is in the range of 1.48 to 1.60, and it is even more desirable if in the range of 1.49 to 1.59. Regarding controlling the refractive index to be in the ranges described above, it is possible to raise the refractive index by increasing the amount added of at least one of the alkaline metal compounds and the alkaline earth metal compounds, or by elevating the heat treatment temperature or by extending the heat treatment time, in the production method described below.

In particular, the curable composition for forming a cured product for dental use preferably has a spherical crystallization control powder content in the range of 55 to 95 mass % and contains at least one of an acrylate monomer and a methacrylate monomer as a polymerizable monomer. In this case, by having an inorganic powder content of at least 55 mass %, sufficient strength and durability as a false tooth or dental prostheses are conferred to the cured product. In addition, acrylate monomers and methacrylate monomers have vast track-records of uses as dental materials, and safety is high when applied to a living organism as, for example, a dental material.

The cured product for dental use is formed into a suitable shape such as, for instance, prismatic, cylindrical, placoid, discoid, or the shape of a prosthesis such as a false tooth, an inlay or a crown. From among these prismatic, cylindrical, placoid, discoid and the like cured products for dental use, for instance, dental prostheses such as false teeth, inlays and crowns are fabricated by milling with, for example, a CAD/CAM machine.

In the following, methods for forming a cured product for dental use, in particular, will be described. When a curable composition is given a photo irradiation, a heat or both the photo radiation and heat adapting to the curable composition, the curable composition is polymerized and cured. A cured product for dental use is obtained in so doing.

For instance, when the curable composition contains an initiator of the heat polymerization type, first, a molding tool having a cavity that is suitably shaped, such as prismatic, cylindrical, placoid, discoid, or in the shape of a prosthesis such as a false tooth, an inlay or a crown, is filled with the curable composition in the cavities, then, the pressure is reduced inside this cavity to remove air bubbles from the curable composition. Next, in a state in which the cavity is closed by having a lid placed on this molding tool, the curable composition is heated under applied pressure or under ordinary pressure to be polymerized and cured. A cured product for dental use is obtained in so doing. The applied pressure and the heating temperature during polymerization and curing may be varied with time in accordance with need.

When the curable composition contains an initiator of the photopolymerization type, for instance, first, a molding tool having a cavity that is suitably shaped, such as prismatic, cylindrical, placoid, discoid, or in the shape of a prosthesis such as a false tooth, an inlay or a crown, and a lid, in which there is a portion that can let light through, are prepared. After the cavity of this molding tool is filled with the curable composition, the pressure is reduced inside this cavity to remove air bubbles from the curable composition. Next, in a state in which a lid has been placed on this molding tool, the curable composition is irradiated with light under applied pressure or under ordinary pressure. In so doing, the curable composition is polymerized and cured, and a cured product for dental use is obtained. During polymerization and curing, as necessary, a heat treatment may be performed as a post-curing treatment on the curable composition after light irradiation.

While there is no limitation as the quality of the material for the molding tool and the lid in which there is a portion that can let light through, for instance, stainless, Teflon (registered trademark), silicone, glass, PET, polycarbonate and the like, may be cited. It is desirable that a treatment is performed on the surfaces of the molding tool and the lid, such as attaching a mold-release.

While the curable composition is suitable for forming a cured product for dental use, it is also applicable to electronic material applications, such as sealant, adhesive, and laminated plate forming material.

EXAMPLES

Powder Preparation (Powder A)
Using oxygen as carrier gas, LPG was burned at a ratio versus oxygen (volume ratio) of 1.1 to generate a flame of approximately 2,000° C. The pulverized powder of natural silica stone (99.9% pure) with an average particle size of 2.0 μm was introduced into this flame to obtain amorphous silica particles with an average particle size of 2.2 μm. To 100 parts by mass of this amorphous silica particle, 4.2 parts by mass of calcium nitrate tetrahydrate (1.00 part by mass in terms of oxide) was added, ethanol was further added and mixed in a ball mill for 30 minutes. After ethanol was removed from this mixture, a heat treatment at 1,100° C. for 24 hours was performed to obtain powder A.

(Powder B)

Powder B was obtained with conditions similar to the case where powder A was prepared, except that the amount of calcium nitrate tetrahydrate added was changed to 2.1 parts by mass (0.50 parts by mass in terms of oxide).

(Powder C)

Using oxygen as carrier gas, LPG was burned at a ratio versus oxygen (volume ratio) of 1.1 to generate a flame of approximately 2,000° C. The pulverized powder of natural silica stone (99.9% pure) with an average particle size of 4.4 μm was introduced into this flame to obtain amorphous silica particles with an average particle size of 4.9 μm. To 100 parts by mass of this amorphous silica particle, 0.8 parts by mass of calcium nitrate tetrahydrate (0.20 parts by mass in terms of oxide) was added, distilled water was further added and mixed in a ball mill for 30 minutes. After distilled water was removed from this mixture, a heat treatment at 1,100° C. for 24 hours was performed to obtain powder C.

(Powder D)

The amorphous silica particles obtained by the flame fusion method during preparation of powder A, not heat-treated and with an average particle size 2.2 μm served as powder D.

[Powder Evaluation]

(Composition)

For powders A to D, the composition in each of the powders A to D was determined by carrying out elemental analysis by the fluorescence x-ray method (JIS R2216: "Fluorescence x-ray analysis of refractory bricks and refractory mortars").

(Relative Background Level)

The powders A to D were filled into glass holders, and the powder x-ray diffraction spectrum of each of the powders A to D was measured using the Kα beam from Cu with an automatic x-ray diffractometer (Model No. RINT2500) manufactured by Rigaku Corporation. The obtained diffraction spectrum was smoothed by the methods described in the literature (Abraham Savitzky et. al., Analytical Chemistry, 36 (8), 1627 (1964)) with the condition of 25 points. Next, the background portion of the diffraction spectrum was extracted by methods described in the literature (Sonneveld, E. J and Visser, J. W., J. Appl. Cryst. 8, 1 (1975)) with the conditions of 40 points interval and 32 times iterations. Based on the results thereof, background level (F) of the powder was calculated based on the above mathematical formula (1).

Meanwhile, using a standard alumina powder (National Institute of Standard & Technology, Standard Reference Material 674a) as a standard sample, powder x-ray diffraction spectrum of this standard alumina powder was measured with the same conditions as in the case of powders A to D. Furthermore the background level (A) of the standard alumina powder was calculated by the same method as in the case of powders A to D.

The relative background levels (F/A) of powders A to F were calculated by dividing the background levels (F) of powders A to D calculated as described above by the background level (A) of the standard alumina powder.

(Average Particle Size)

The D50 (median particle size where the accumulation of volume is 50% of the total cumulative volume) of powders A to D was measured by the laser diffraction/dispersion method using Model No. LA-920 manufactured by HORIBA, Ltd. During this measurement, particles were dispersed in ion-exchanged water by applying ultrasound, and the average particle size was measured in a state where the transmittance of the dispersion thus obtained was 80 to 90%. No relative refractive index was used for the measurements.

(Sphericity)

The powders A to D were observed using Real Surface View microscope (model No. VF-7800) manufactured by KEYENCE CORPORATION, and for 50 arbitrary particles, the surface area of the particle projection cross-section and the perimeter length of this cross-section were measured from the obtained images. Next, the respective (circumferential length of a true circle of the same surface area as the surface area of a particle projection cross-section)/(measurement value of the perimeter length of the particle projection cross-section) values were derived for the 50 particles, and the mean value of the obtained values served as sphericity.

(Refractive Index)

The refractive index of each of the powders A to D was determined by the method B (immersion method using a microscope (Becke line method)) among the JIS K7142 "Methods for the determination of refractive indices of plastics".

(Results)

The above results are shown in the following Table 1.

TABLE 1

|  | Crystallization promoter | | Composition $SiO_2$ (mass %) | Relative background level | Mean particle size (μm) | Sphericity | Refractive index |
| --- | --- | --- | --- | --- | --- | --- | --- |
|  | Species | Amount added* (parts by mass) | | | | | |
| Powder A | Calcium nitrate | 1.00 | 98.9 | 4.2 | 2.8 | 0.96 | 1.55 |
| Powder B | Calcium nitrate | 0.50 | 99.4 | 5.8 | 2.4 | 0.98 | 1.53 |
| Powder C | Calcium nitrate | 0.20 | 99.7 | 6.7 | 5.6 | 0.98 | 1.52 |
| Powder D | — | 0.00 | 99.9 | 24 | 2.2 | 0.98 | 1.44 |

*Amount added in terms of oxide with respect to 100 parts by mass of amorphous silica particle Examples 1 to 5, Comparative Example 1

Preparation of Curable Composition and Cured Product

In each example and comparative example, a curable composition was obtained by stir-mixing the constituents indicated in the following Table 2. In Table 2, TEDM represents triethyleneglycol dimethacrylate, PGA-HMU represents di(phenylglycidylether acrylate)-hexamethylene diurethane, TMPTM represents trimethylolpropane trimethacrylate, and BPO represents benzoylperoxide, respectively. A surface treatment was performed on powders A to D prior to mixing, by pre-spraying a silane coupling agent (γ-methacryloxypropyl trimethoxysilane) and then stirring. The amount of silane coupling agent used was 0.3 parts by mass with respect to 60 parts by mass of powder.

In Examples 1, 2, 4 to 5 and Comparative Example 1, a curable composition was filled into a stainless molding tool (two types of cavity sizes: 50 mm×40 mm×2 mm and 50 mm×40 mm×1 mm), degassed by reduced pressure, and then a stainless lid was fitted onto this molding tool. In this state, the curable composition was cured by being heated at 80° C. for 1 hour and then heated at 120° C. for 1 hour to obtain a cured product.

In Example 3, a curable composition was filled into a molding tool made of a glass plate and a stainless frame (two types of cavity sizes: 50 mm×40 mm×2 mm and 50 mm×40 mm×1 mm), degassed by reduced pressure, and then a stainless lid was fitted onto this molding tool. In this state, a 365 nm UV light with an intensity of 100 mW/cm$^2$ was irradiated for 5 minutes from a dental photopolymerization device towards the curable composition through a glass surface on one side of the molding tool and then was irradiated for 5 minutes through the glass surface on the opposite side of the molding tool. In so doing, the curable composition was cured to obtain a cured product.

A test piece was cut out from the cured product obtained in each of the examples and comparative examples, and evaluation tests of this test piece were carried out by the methods described in the following.

(Bending Strength Test (Normal State))

The dimensions of the test piece were 25 mm×2 mm×2 mm, and the strength at break of this test piece was measured using a bending testing machine at 1 mm per minute cross-head speed. In each example and comparative example, measurements were performed on 5 test pieces, and evaluation was by the mean value of the results thereof. This value served as a representative value for the strength of the cured product.

(Bending Strength Test (after Water Immersion))

The dimensions of the test piece were 25 mm×2 mm×2 mm, and this test piece was first immersed in water at 37° C. for 24 hours. Next, the strength at break of this test piece was measured using a bending testing machine at 1 mm per minute cross-head speed. In each example and comparative example, measurements were performed on 5 test pieces, and evaluation was by the mean value of the results thereof. This value served as a representative value for the durability of the cured product.

(Refractive Index Difference)

In each example and comparative example, a curable composition was prepared without mixing powders A to D, and this curable composition was cured to obtain a cured product (partially cured product). The refractive index of this partially cured product was determined by the A method (measurement method using an Abbe refractometer) among the JIS K7142 "Methods for the determination of refractive indices of plastics". For each example and comparative example, the difference between the refractive index of this partially cured product and the refractive index of the powder was calculated.

(Transparency Test)

The dimensions of the test piece were 13 mm×13 mm×1 mm. This test piece was buffed until the thickness reached 0.8 mm. The total light transmittance of this test piece was measured with a hazemeter, with the total light transmittance of the air space being 100%. In each example and comparative example, measurements were performed on 3 test pieces, and evaluation was by the mean value of the results thereof. This value served as a representative value for the aesthetic quality of the cured product.

(Evaluation Results)

The above results are shown in the following Table 2.

TABLE 2

| | | | Example | | | | | Comparative example |
|---|---|---|---|---|---|---|---|---|
| | | | 1 | 2 | 3 | 4 | 5 | 1 |
| Powder species | | | A | B | B | B | C | D |
| Composition (parts by mass) | Powder | | 60 | 60 | 60 | 60 | 60 | 60 |
| | TEDM | | 20 | 20 | 20 | 14 | 20 | 20 |
| | PGA-HMU | | 20 | 20 | 20 | 13 | 20 | 20 |
| | TMPTM | | — | — | — | 13 | — | — |
| | BPO | | 0.3 | 0.3 | — | 0.3 | 0.3 | 0.3 |
| | Camphorquinone | | — | — | 0.4 | — | — | — |
| Evaluation | Bending strength test (normal state) | MPa | 167 | 163 | 162 | 156 | 163 | 160 |
| | Bending strength test (after water immersion) | MPa | 155 | 153 | 146 | 144 | 154 | 151 |
| | Refractive index of partially cured product | | — | 1.53 | 1.53 | 1.53 | 1.52 | 1.53 | 1.53 |

TABLE 2-continued

|  |  | Example | | | | | Comparative example |
|---|---|---|---|---|---|---|---|
|  |  | 1 | 2 | 3 | 4 | 5 | 1 |
| Refractive index difference | — | 0.02 | 0.00 | 0.00 | 0.01 | 0.01 | 0.09 |
| Transparency test | % | 55 | 68 | 67 | 66 | 62 | 30 |

The cured product obtained in each example demonstrated sufficient strength, durability and aesthetic quality. When used as dental materials such as teeth crown material, prosthetic material and artificial teeth for dental use, these cured products have excellent properties as substitution materials for natural teeth.

The invention claimed is:

1. A curable composition containing an inorganic powder and a polymerizable monomer,
wherein the inorganic powder contains a spherical crystallization control powder,
the spherical crystallization control powder has a silicon dioxide content of 98.9 mass % or greater but 100 mass % or less,
a non-crystalline portion and a crystalline portion are mixed within the spherical crystallization control powder,
a refractive index difference is 0.05 or less between the spherical crystallization control powder and a cured product obtained by curing only constituents after removal of the spherical crystallization control powder from the curable composition, and
the polymerizable monomer includes at least one of an acrylate monomer and a methacrylate monomer, and the spherical crystallization control powder content is in a range of 55 to 95 mass %.

2. The curable composition according to claim 1, wherein a refractive index of the spherical crystallization control powder is in a range of 1.48 to 1.60.

3. The curable composition according to claim 1, wherein a relative background level of the spherical crystallization control powder in an x-ray diffraction spectrum is 3 to 10.

4. The curable composition according to claim 1, wherein an average particle size of the spherical crystallization control powder is in a range of 0.01 to 50 μm.

5. The curable composition according to claim 1, wherein the spherical crystallization control powder is obtained by partially crystallizing, through heat treatment, amorphous spherical particles obtained by a flame fusion method.

6. The curable composition according to claim 1, further containing a polymerization catalyst, wherein the spherical crystallization control powder content is in a range of 5 to 95 mass %.

7. A cured product for dental use obtained by curing the curable composition according to claim 1.

8. A process for producing a cured product for dental use, the process comprising:
forming the curable composition as defined in claim 1 to the cured product for treatment of a tooth.

* * * * *